United States Patent [19]
Ueda et al.

[11] Patent Number: 5,286,627
[45] Date of Patent: Feb. 15, 1994

[54] METHOD OF HIGH-SENSITIVE ANALYSIS OF BILE ACID AND REAGENT COMPOSITION FOR THE ANALYSIS

[75] Inventors: Shigeru Ueda, Shizuoka; Masashi Tanno, Mishima; Hideo Misaki, Shizuoka, all of Japan

[73] Assignee: Asahi Kasei Kogyo Kabushiki Kaisha, Osaka, Japan

[21] Appl. No.: 510,716

[22] Filed: Apr. 18, 1990

[30] Foreign Application Priority Data

Apr. 18, 1989 [JP] Japan .................................. 1-98443

[51] Int. Cl.$^5$ .......................... C12Q 1/32; C12Q 1/26; C12N 9/02; C12N 9/08
[52] U.S. Cl. ...................................... 435/26; 435/25; 435/189; 435/810
[58] Field of Search ........................... 435/25, 26, 14.4

[56] References Cited

U.S. PATENT DOCUMENTS

| | | | |
|---|---|---|---|
| 4,310,624 | 1/1982 | Modrovich | 435/4 |
| 4,490,465 | 12/1984 | Limbach et al. | 435/14 |
| 4,556,634 | 12/1985 | Misaki et al. | 435/25 |
| 4,622,296 | 11/1986 | Yamanishi et al. | 435/26 |
| 4,629,697 | 12/1986 | Limbach et al. | 435/26 |
| 4,791,057 | 12/1988 | Misaki et al. | |
| 4,816,394 | 3/1989 | Ushizawa et al. | 435/26 |
| 4,874,696 | 10/1989 | Payne et al. | |
| 4,889,801 | 12/1989 | Ushizawa | 435/25 |

FOREIGN PATENT DOCUMENTS 0245528 11/1988 European Pat. Off.

OTHER PUBLICATIONS

Mushigue et al. Clin. Chim. Act. 70:79 (1976).
Patent Abs. of Jap. vol. 6 (127): C-113 (1982).
Mashige et al., Clin. Chem. 24(7):1150–54, (1978).
Mashige et al., Clin. Chim. Acta 70: 79–86 (1976).
Chen-L-J, Anal. Biochem. 105: 170–173 (1980).
Anwer et al. Analytical Biochem, 99(2): 408–14 (1979).
Palmer, R. in Methods in Enzymology vol. XV. Sec. I pp. 280–289 (1969).
Nicolas et al. Anal. Biochem 103 (1): 170–75 (1980).
Zubay, G. Biochemistry, Addison-Wesley Pub. Co. 211–212 (1984).

(List continued on next page.)

Primary Examiner—Robert A. Wax
Assistant Examiner—Miguel J. Escallon
Attorney, Agent, or Firm—Young & Thompson

[57] ABSTRACT

A method for a high-sensitivity quantitative analysis of bile acid in a bile acid-containing sample utilizes a reagent comprising:
(1) a steroid dehydrogenase which is capable of effecting a reversible reaction producing oxobile acid using bile acid, as a substrate, and a nicotinamide adenine dinucleotide phosphate compound (hereinafter referred to as an NADP compound) or a nicotinamide adenine dinucleotide compound (hereinafter referred to as an NAD compound) as coenzyme;
(2) a compound $A_1$ selected from the group consisting of NADP compounds and NAD compounds, in an amount surplus relative to the amount of bile acid;
(3)
  (i) compound $B_1$ selected from the group consisting of a reduced NAD compound and a reduced NADP compound, compound $B_1$ being a reduced NAD compound, when $A_1$ is an NADP compound, and a reduced NADP compound, when $A_1$ is an NAD compound, or
  (ii) a compound $B_2$ which is an oxidized product of $B_1$, or
  (iii) a mixture of $B_1$ and $B_2$, where the amount of $B_1$ plus $B_2$ is less than 1/100 of the molar amount of $A_1$, and
  (iv) a second dehydrogenase which does not react with bile acid and compound $A_1$, but does effect a reaction converting compound $B_2$ into compound $B_1$, and the substrate of the second dehydrogenase.

18 Claims, 5 Drawing Sheets

OTHER PUBLICATIONS

Tamasawa et al. CAbs. vol. 108:108:91236u (1988).
Ikawa et al Chem. Abs. vol. 95:#76434b (1981).
Stephen et al J. of Lipi Res. 19:924 (1978).
Chaintreul et al. Colloquie Int. Ann Biol. Clin 36:149 (1978).
Patent Abstracts of Japan, vol. 6, No. 127 (C-113) [1005], 13th Jul. 1982; & JP-A-57 54 598 (Mamoru Sugiura) Jan. 4, 1982.
J. Org. Chem., vol. 51, 1986, pp. 2902-2906; S. Riva et al.: "Preparative-scale regio- and stereospecific oxidoreduction of cholic acid and dehydrocholic acid catalyzed by hydroxysteroid dehydrogenases".
Proceedings of the 33rd Annual Meeting of the Japan Society of Clinical Pathology, Supplement vol. 34, 1986, p. 123.
Proceedings of the 33rd Annual Meeting of the Japan Society of Clinical Pathology, Supplement vol. 35, 1987, p. 124.
Japanese Patent Publication No. 37658/1988 (Abstract).
Japanese Patent Publication No. 13197/1984 (Abstract).

METHOD OF HIGH-SENSITIVE ANALYSIS OF BILE ACID AND REAGENT COMPOSITION FOR THE ANALYSIS

BACKGROUND OF THE INVENTION

1. Field of the Invention

This invention relates to a method of high-sensitive analysis of bile acid, especially bile acid in living body samples.

2. Description of the Background Art

Analysis of bile acid in samples taken from living bodies, such as serum and the like, is important for clinical diagnosis of liver functions as well as for elucidating the cause of such diseases as jaundice, cholelithiasis, and the like.

Conventionally, various methods have been reported for the analysis of bile acid containing cholic acid, deoxycholic acid, chenodeoxycholic acid, and the like. One of the methods recently used for clinical diagnosis involves the use of 3α-hydroxysteroid dehydrogenase and, as a coenzyme, either a nicotinamide adenine dinucleotide compound (hereinafter referred to as NAD) or a nicotinamide adenine dinucleotide phosphate compound (hereinafter referred to as NADP). Reduced NAD (hereinafter referred to as NADH) or reduced NADP (hereinafter referred to as NADPH) produced in an amount in proportion to the amount of bile acid is then quantitatively measured (Japanese Patent Publication No. 13197/1984). The method, however, is liable to be influenced by bilirubin, and thus requires separation of bile acid in advance. This, in turn, requires a large amount of samples for the analysis. Another drawback of this method is in its low sensitivity. The use of high-sensitivity coloring agents has been proposed in order to overcome this drawback [Proceedings of the 33th of Annual Meeting of Japan Society of Clinical Pathology, 123 (1986); ibid., the 34th Annual Meeting, 124 (1987)]. This method, however, does not bring about a complete solution to the problem.

Another method comprises converting 3-oxosteroid produced into 3-oxo-Δ4-steroid by the action of 3-oxo-Δ4-steroid dehydrogenase for producing formazan twice as much as an amount in conventional method for colorimetric determination. A kit for carrying out this method is commercially available. This method, however, brings about no more effects than making the sensitivity twice as much as that obtained from conventional method.

Japanese Patent Publication No. 36758/1988 discloses a method for the analysis of bile acid by means of an enzymatic cycling reaction of NADH or NADPH which is produced in an amount proportionate to the amount of bile acid. In order to increase the amount of NADH or NADPH by an enzymatic cycling reaction for obtaining a better sensitivity in the analysis, this method requires a step of eliminating surplus NAD or NADP by decomposition with heating in an alkali. Since this involves a complicated procedure, the method is disadvantageous when applied to clinical investigation purposes which require analysis of a large number of samples.

In view of this situation, the present inventors have undertaken extensive studies about the mechanism of the reversible reaction in which oxobile acid is produced using bile acid as a substrate. As a result, the inventors discovered that steroid dehydrogenases derived from normal microorganisms reacted with NADs as conenzymes but hardly reacted with NADPs, and further that a commercially available 3α-hydroxysteroid dehydrogenase [produced by Toyo Jozo Co., Ltd. "Enzyme Catalog" No. T-27, page 53)] derived from Pseudomonas sp. B-0831 (FERM BP-2376) belonging to the genus Pseudomonas reacted with both NAD and NADP compounds as coenzymes.

Furthermore, the present inventors have found that when a reversible cycling reaction was carried out in a reaction system in which oxobile acid is produced from bile acid using the above steroid dehydrogenase, and an NAD compound or an NADP compound, respectively, as a coenzyme, in the presence of an NADPH compound or an NADH compound, respectively, the amount of NADH or NADPH produced linearly increased over time and its rate of increase was proportionate to the amount of bile acid.

These findings have led to the completion of the present invention.

SUMMARY OF THE INVENTION

Accordingly, an object of this invention is to provide a method of high-sensitive analysis of bile acid comprising:

reacting a bile acid-containing sample with a reagent comprising:

(1) a steroid dehydrogenase which is capable of effecting a reversible reaction producing oxobile acid using bile acid as a substrate, in which reaction a nicotinamide adenine dinucleotide phosphate compound (hereinafter referred to as NADP) or a nicotinamide adenine dinucleotide compound (hereinafter referred to as NAD) are to be used as coenzymes, (2) Compound $A_1$ (defined hereinbelow) in an amount surplus relative to the amount of bile acid, (3) Compound $B_1$ (defined hereinbelow) or compound $B_2$ (defined hereinbelow), or both, and (4) a second dehydrogenase which does not react with bile acid and compound $A_1$, but effects the reaction converting compound $B_2$ into compound $B_1$, and the substrate of the second dehydrogenase, to effect the following reaction,

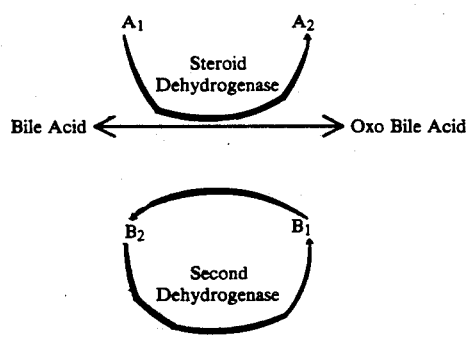

wherein $A_1$ is a NADP or a NAD, $A_2$ is a reduced product of $A_1$, $B_1$ is a reduced NAD when $A_1$ is a NADP and a reduced NADP when $A_1$ is a NAD, $B_2$ is a oxidized product of $B_1$, $B_2 \rightarrow B_1$ indicates a reaction producing $B_1$ using $B_2$ as a coenzyme, and measuring the amount of $A_2$ in the above reaction.

Another object of the invention is to provide a reagent composition for the an of bile acid comprising:

(1) a steroid dehydrogenase is capable of effecting a reversible reaction producing oxobile acid using bile acid as a substrate, in a nicotinamide adenine dinucleotide phosphate (NADP) or a nicotinamide adenine dinucleotide compound (NAD) are to be used as coenzymes, (2) compound $A_1$ in an amount surplus relative to the amount of bile acid, (3) compound $B_1$ or compound $B_2$, or both, and (4) a second dehydrogenase which does not react with bile acid and compound $A_1$, but effects the reaction converting compound $B_2$ into compound $B_1$, and the substrate of the second dehydrogenase.

Other objects, features and advantages of the invention will hereinafter become more readily apparent from the following description.

DETAILED DESCRIPTION OF THE INVENTION AND PREFERRED EMBODIMENTS

Figure 1:
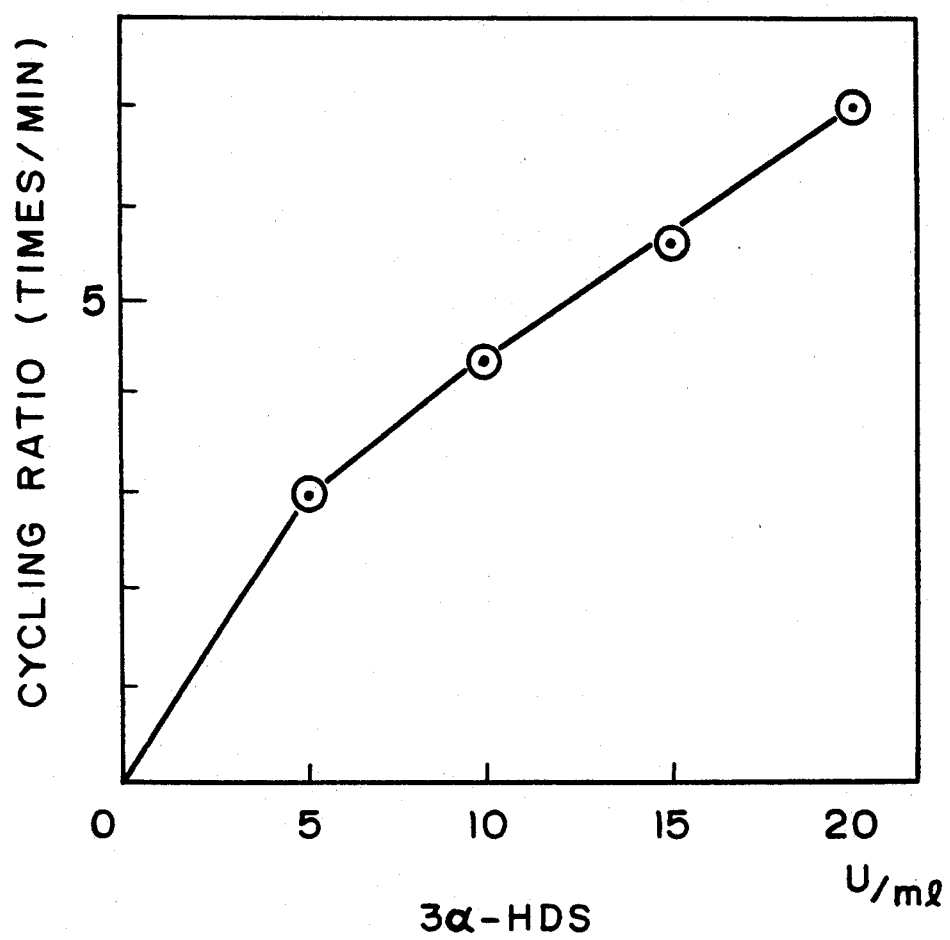
FIG. 1 is a diagram showing the relationship between the amount of 3α-HSD and the cycling ratio.

Any steroid dehydrogenases satisfying the above requirements can be used for the purpose of the present invention. Specific examples are commercially available 3α-hydroxysteroid dehydrogenase (3α-HSD) which are derived from Pseudomonas sp., B-0831, 7α-HSD, 12α-HSD, and the like.

Given as examples of NADP and NAD compounds represented by $A_1$ and $B_2$ are nicotinamide adenine dinucleotide phosphate (NADP), acetylpyridine adenine dinucleotide phosphate (acetyl NADP), nicotinamide hypoxanthine dinucleotide phosphate (deamino NADP), and the like for NADPs; and nicotinamide adenine dinucleotide (NAD), acetylpyridine adenine dinucleotide (acetyl NAD), nicotinamide hypoxanthine dinucleotide (deamino NAD), and the like for NADs. The $A_1$ and $B_2$ must be different from each other. When $A_1$ is a NADP compound, $B_1$ is a reduced NAD compound, when $A_1$ is a NAD compound, $B_1$ is a reduced NADP compound.

It is essential that the amount of $A_1$ be surplus in relation to the amount of bile acid. The amount of $A_1$ 20 to 10,000 times of mol of bile acid is especially preferable. It is also essential that the amount of $B_1$ is smaller than $A_1$. A preferable amount of $A_1$ is smaller than 1/100 mol of $B_1$. $B_2$ can be used instead of $B_1$.

Given as examples of second dehydrogenases and their substrates are, when $B_1$ is a NAD compound, alcohol dehydrogenase (EC 1.1.1.1) and ethanol, glycerol dehydrogenase (EC 1.1.1.6) derived from E. Coli and glycerol, glycerol-3-phosphate dehydrogenase (EC 1.1.1.8) derived from rabbit muscle and L-glycerol-3-phosphate, malic acid dehydrogenase (EC 1.1.1.37) derived from porcine cardiac muscle and L-malic acid, glyceroaldehyde phosphate dehydrogenase (EC 1.2.1.12) derived from rabbit skeletal muscle, liver, yeast, or E. Coli, D-glyceraldehyde phosphate, and phosphoric acid; and when $B_1$ is a NADP compound, glucose-6-phosphate dehydrogenase (EC 1.1.1.49) derived from yeast and glucose-6-phosphate, iso-citric acid dehydrogenase (EC 1.1.1.42) derived from porcine cardiac muscle or yeast and iso-citric acid, glyoxylic acid dehydrogenase (EC 1.2.1.17) derived from Pseudomonas oxalaticus, CoA, and glyoxylic acid, phosphogluconic acid dehydrogenase (EC 1.1.1.44) derived from rat liver, beer yeast, or E. coli and 6-phospho-D-gluconic acid, glyceraldehyde phosphate dehydrogenase (EC 1.2.1.13) derived from plant chlorophyll, D-glyceraldehyde-3-phosphate, and phosphoric acid, benzaldehyde dehydrogenase (EC 1.2.1.7) derived from Pseudomonas fluorescens and benzaldehyde, and the like.

In the reagent composition for the analysis of bile acid of the present invention, a concentration of component $A_1$ may be 0.05 to 100 mM, and preferably 2 to 30 mM. The concentration of $B_1$ and/or $B_2$ is suitably determined based on the amount of $A_1$, i.e., the amounts of $B_1$ plus $B_2$ is less than 1/100 mol of the amount of $A_1$, for example, 0.05 to 500 μM, and preferably 5 to 50 μM. The amount of steroid dehydrogenase may be, for example, 0.05 to 100 U/ml, and preferably 1 to 50 U/ml. The amount of second dehydrogenase is 20 times or more of the Km value for $B_2$, and, for example, 1 to 100 U/ml. The substrate for the second dehydrogenase is used in an amount of, for example, 0.5 to 50 mM, and preferably 0.5 to 30 mM. The use of the substrate exceeding this amount is acceptable.

Any steroid dehydrogenases can be used which are reactive with a bile acid reagent such as cholic acid acting as a substrate in the presence of a NAD compound preferably, nicotinamide adenine dinucleotide (NAD), and a NADP compound preferably, nicotinamide adenine dinucleotide phosphate (NADP), as a coenzyme. Applicability of a steroid dehydrogenase to the reagent of the present invention can be confirmed by the use of such a coenzyme and a substrate to be used. In the case of commercially available steroid dehydrogenase, e.g. 3α-HSD (produced by Toyo Jozo Co., Ltd. "Enzyme Catalog" No. T-27, page 53), the Km values in the reaction with NAD and cholic acid are $2.9 \times 10^{-5}$ M and $3 \times 10^{-5}$ M, respectively, and in the reaction with NADP and cholic acid are $1.14 \times 10^{-4}$ M and $6.2 \times 10^{-5}$ M, respectively. The pH in the forward reaction of NAD or NADP and cholic acid is in the neighborhood of 9.5, and the optimum pH of the reversible reaction of NADH or NADPH and oxocholic acid is in the neighborhood of 5.5. In the actual reaction, the pH is adjusted based on the Km value for each coenzyme so that the ratio of forward reaction rate and reversible reaction rate may be close to 1. An example of other 3α-HSD which can be used for the same purpose is that of EC 1.1.1.50 [J. Steroid Biochem, 8, 41–46 (1977)] derived from rat liver or rat prostate. These enzymes can be used independently or two or more may be used together.

In order to bring the ratio of the forward/reverse reaction rate as close as to 1, a reagent which can accelerate either the forward or reverse reaction of which the rate is lower than the other may be added. For instance, when the forward reaction rate is retarded by the adjustment of pH conditions, another steroid dehydrogenase which can promote the forward reaction may be added. On the other hand, when the reverse reaction rate is lower, other steroid dehydrogenase which can accelerate the reverse reaction may be added. A compound which can function as a coenzyme for either of the NAD or NADP compound can be used as such a steroid dehydrogenase to be added to adjust the rate of the reaction. Examples of such enzymes are those accelerating the reaction of bile acid to oxobile acid in the presence of a NAD or NADP, and those accelerating the reaction of oxobile acid to bile acid in the presence of a NADH or NADPH. Appropriate enzymes can be selected from published enzyme lists. Examples are NAD specific 3α-HSD derived from *Bacillus sphaericus* (Japanese Patent Application Laid-open No. 157894/1979), 3α-HSD derived from *Pseudomonas testosteroni* [J. B. C., 227, 37–52 (1957)], and the like.

For the determination of an amount of bile acid in a sample using the reagent prepared as described above and according to the method of the present invention, 0.001 to 0.5 ml of the sample is added to the reagent containing above components (1) to (4) at pH 8–10 and reacted at about 37° C. The amount of $A_2$ produced by the reaction is then determined by measurement of absorption for the prescribed period of time, several minutes to several tens of minutes, at two prescribed times after start of the reaction, e.g. for 1 minute at 3 minute and 4 minute after start of the reaction, or for 5 minutes at 3 minute and 8 minute after start of the reaction. Absorption is measured at 340 nm, for example, when $A_2$ is a NADH or NADPH. The amount of bile acid in the sample can easily be determined from the difference of the two absorption measurements. This two-point absorption determination also allows to omit the blank assay of the sample. Besides analysis by means of absorption measurement, the amount of $A_2$ produced can be determined by known analytical methods, for example, by the method using diaphorase and tetrazolium salts, the method using resazurin, or the like.

As illustrated above, the method of the present invention can greatly promote the sensitivity through combination with an enzymatic cycling reaction. The method ensures prompt and accurate determination of bile acid using a small amount of sample.

Other features of the invention will become apparent in the course of the following description of the exemplary embodiments which are given for illustration of the invention and not intended to be limiting thereof.

EXAMPLES

Example 1

Reagent 40 mM glycine-NaOH (pH 10.0)
5 mM NADP
20 μM NADH
0.4M ethanol
30 U/ml alcohol dehydrogenase (produced by Oriental Yeast Co.)
10 U/ml 3α-HSD (derived from Pseudomonas sp., produced by Toyo Jozo Co., Ltd.)
0.2% Triton X-100

Procedure 1 ml of the above reagent was taken into a quartz cuvette and 2 nmol of cholic acid was added to it. A time course was measured at 340 nm on NADPH produced. A reagent without the addition of cholic acid was used as a control. The results are shown in Table 1.

TABLE 1

| Time (minutes) after start of reaction | OD ($A_{340}$) value | |
|---|---|---|
| | 2 nmol cholic acid | Control |
| 0 | 0.301 | 0.303 |
| 1 | 0.348 | 0.305 |
| 2 | 0.405 | 0.307 |
| 3 | 0.464 | 0.310 |
| 4 | 0.521 | 0.313 |
| 5 | 0.580 | 0.317 |
| 6 | 0.637 | 0.320 |
| 7 | 0.696 | 0.323 |
| 8 | 0.753 | 0.327 |
| 9 | 0.811 | 0.330 |
| 10 | 0.868 | 0.332 |

The results of the table shows that the absorption at 340 nm increased linearly at least during the 10 minute reaction.

The cycling rate (cycle/minute) of the reaction was calculated according to the following equation.

$$\frac{\Delta A_s - \Delta A_b}{t} \times \frac{1}{6.22} \times \frac{1}{2}$$

wherein t is the reaction time (minute), $\Delta A_s$ is the change in absorption at 340 nm (mAbs) at reaction time t of the reaction mixture to which cholic acid was added, $\Delta A_b$ is the change in absorption at 340 nm (mAbs) at reaction time t of the control, 6.22 is the molar extinction coefficient (cm$^2$/μmol) of NADPH at 340 nm, 1 is the total amount (ml) of the reagent used, and 2 is the amount (nmol) of cholic acid added.

The results of the test demonstrates that the sensitivity in the 10 minute reaction was promoted about 44 times.

The same measurements were carried out by changing the amount of 3α-HSD in the reagent within the range of 0 to 20 U/ml. The relationship between the amount of 3α-HSD and the cycling ratio (cycle/minute), determined by the above equation, is given in FIG. 1, which shows that the cycling ratio at a 3α-HSD concentration of 20 U/ml is about 7 cycle/minute. This is the evidence that the cycling ratio can be suitably adjusted depending on the amount of 3α-HSD used.

Example 2

Figure 2:
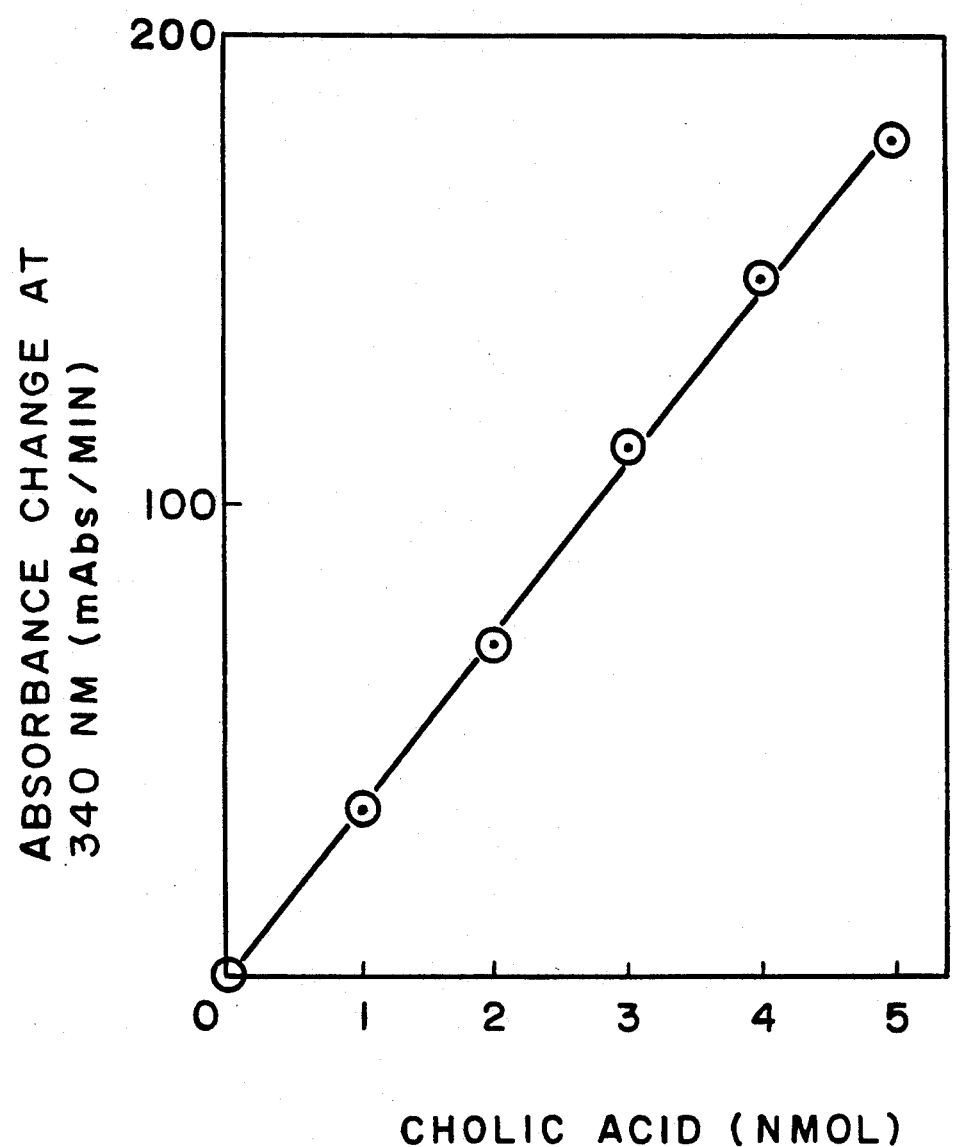
FIG. 2 shows the result of the rate assay of the amount of cholic acid at 340 nm.

Reagent 40 mM glycine-NaOH (pH 10.0)
5 mM NADP
20 μM NADH
0.4M ethanol
30 U/ml alcohol dehydrogenase
0.2% Triton X-100
10 U/ml 3α-HSD Procedure 1 ml of the above reagent was taken into each quartz cuvette, following which 10 μl of 0.1, 0.2, 0.3, 0.4, and 0.5 mM of cholic acid solutions were added. Mixtures were reacted at a temperature of 37° C. The absorptions at 340 nm at 3 minute and 4 minute after start of the reaction were measured. The difference of the measurements for each sample was determined. The results are given in FIG. 2, which shows that the change in absorption increased linearly in relation to the amount of cholic acid.

Example 3

Reagent 40 mM glycine-NaOH (pH 10.0)
5 mM NADP
20 μM NADH
0.2M ethanol
0.2% Triton X-100
45 U/ml alcohol dehydrogenase
20 U/ml 3α-HSD

Figure 3:
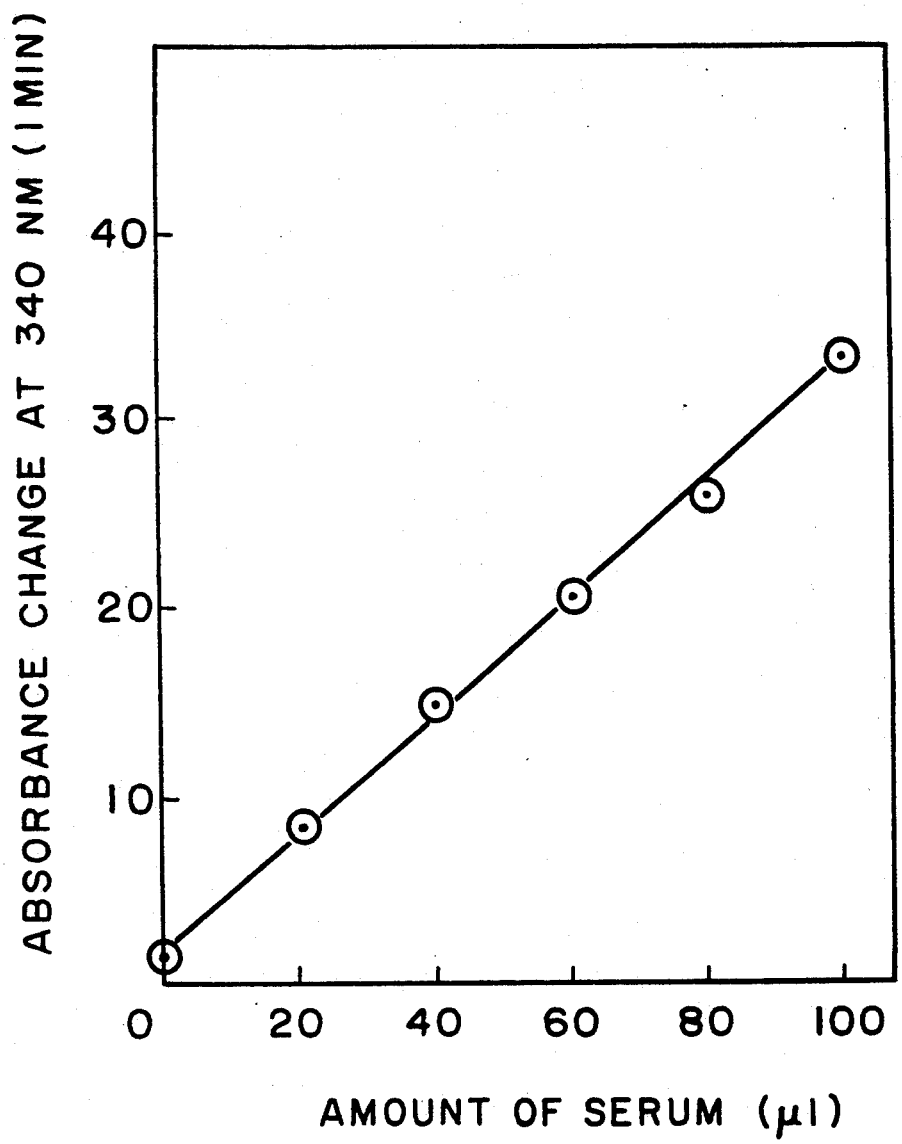
FIG. 3 shows the result of the rate assay of the amount of serum at 340 nm.

Procedure 1 ml of the above reagent was taken into each quartz cuvette, following which 0.20, 40, 60, 80, and 100 μl of serum were added. Mixtures were processed in the same manner as in Example 2. The results are shown in FIG. 3.

Example 4

Figure 4:
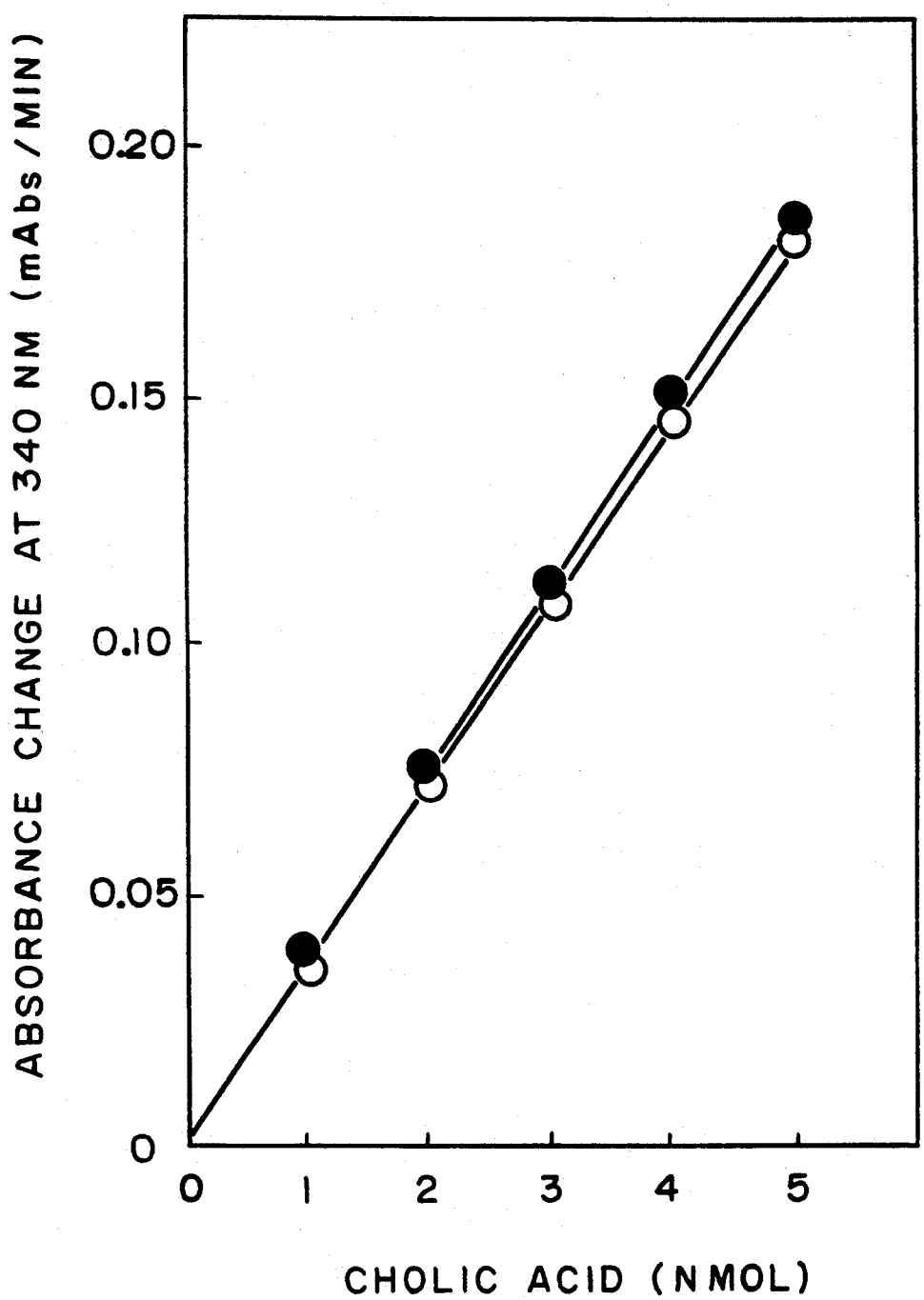
FIG. 4 shows the result of quantitative analysis of cholic acid in serum.

Oxamic acid (LDH inhibitor) was added to the reagent of Example 2 to the concentration of 1 mM. Another sample reagent was prepared by further adding 10 U/ml of 3α-HSD derived from *Pseudomonas testosteroni*. These sample reagents were taken into quartz cuvettes and processed in the same manner as in Example 2. The results are shown in FIG. 4, which shows a linear relationship between the change in absorption and the amount of cholic acid. In FIG. 4, the line linked by open circles is that obtained by using solely commercially available 3α-HSD derived from Pseudomonas sp. B-0831, and the line linked by solid circles is that obtained by using 3α-HSD derived from *Pseudomonas testosteroni* in conjunction with the commercially available 3α-HSD.

Example 5

Oxamic acid (LDH inhibitor) was added to the reagent of Example 2 to the concentration of 1 mM. To this reagent was added 50 μl of serum samples prepared by adding cholic acid to the concentration of 25 μM, 50 μM, or 100 μM. Each mixture was then processed in the same manner as in Example 2. The results are presented in Table 2, which shows that the recovery rates were 98.3 to 101.0%.

TABLE 2

| Cholic acid added (μM) | Cholic acid found (μM) | Difference | Recovery rate (%) |
|---|---|---|---|
| 0 | 18.3 | 0 | |
| 25 | 43.1 | 24.8 | 99.2 |
| 50 | 68.8 | 50.5 | 101.0 |
| 100 | 116.6 | 98.3 | 98.3 |

Example 6

The same experiment as in Example 5 was carried out by using serum samples prepared by adding 200 mg/dl of glucose, 10 mg/dl of uric acid, 20 mg/dl bilirubin, and 5 mg/dl ascorbic acid. The results are presented in Table 3, which shows that these additives hardly affects the measurement.

TABLE 3

| Additive | Amount of Additive (mg/dl) | Bile acid found (μM) | Relative Amount (%) |
|---|---|---|---|
| — | — | 18.4 | 100 |
| Glucose | 200 | 18.6 | 101 |
| Uric acid | 10 | 18.0 | 98 |
| Bilirubin | 20 | 18.0 | 98 |

TABLE 3-continued

| Additive | Amount of Additive (mg/dl) | Bile acid found (μM) | Relative Amount (%) |
|---|---|---|---|
| Ascorbic acid | 5 | 18.8 | 102 |

Example 7

Reproducibility of the analysis of the present invention was investigated by processing two kinds of serum, 50 μl each, using the reagent of Example 2 in the same manner as in Example 2. The results are presented in Table 4.

TABLE 4

| | Amount of bile acid (μmol/l) | |
|---|---|---|
| Test Run No. | Serum I | Serum II |
| 1 | 5.56 | 18.42 |
| 2 | 5.43 | 18.60 |
| 3 | 5.58 | 18.56 |
| 4 | 5.64 | 18.72 |
| 5 | 5.40 | 18.58 |
| 6 | 5.72 | 18.68 |
| 7 | 5.54 | 18.59 |
| 8 | 5.62 | 18.66 |
| 9 | 5.62 | 18.46 |
| 10 | 5.58 | 18.81 |
| Average | 5.57 | 18.61 |
| SD | 0.096 | 0.116 |
| CV (%) | 1.71 | 0.63 |

Example 8

Bile acid contents were measured on 17 serum samples using a commercially available bile acid measuring reagent and the reagent of the present invention.

Total Bile Acid Test Wako (tradename, produced by WAKO ® Pure Chemical Co., containing NAD, 3α-HSD derived from *Pseudomonas testosteroni*, diaphorase, and nitrotetrazolium blue) was used as a commercial reagent. Coenzyme NAD and 3α-HSD were reacted with 200 μl of serum precisely for 10 minutes at 37° C. NADH produced was used to reduce nitrotetrazolium via diaphorase to produce purple red diformazan. The absorption ($E_s$) of purple red color and the absorption ($E_{sb}$) of a sample blank were measured at 560 nm. The total bile acid content in 200 μl of serum sample corresponding to ($E_s - E_{sb}$) value was determined from the calibration curve.

In the bile acid analysis according to the method of the present invention, a reagent containing 40 mM glycine-NaOH (pH 10.0), 5 mM NADP, 20 μM NADH, 0.01% ethanol, 20 U/ml commercial 3α-HSD derived from Pseudomonas sp. B-0831, 0.2% Triton X-100, and 45 U/ml alcohol dehydrogenase was used. 1 ml of the reagent was taken into a quartz cuvette, stirred thoroughly, and heated at 37° C. for 2 minutes. To this 50 μl of the serum sample was added and heated at 37° C. Changes in the absorption ($\Delta E_s$) in 3 minutes at 2-5 minute after the serum addition were measured at 340 nm. A blank measurement ($\Delta E_b$) was made on the reagent to which water was added instead of serum. Absorption was also measured on a standard liquid ($\Delta E_{std}$) using 50 μl of 10 μM glycocholic acid (prepared by diluting the glycocholic acid included in the Total Bile Acid Test WAKO ® reagent to a volume of 5-fold).

The bile acid concentration was determined by the following equation.

Bile Acid Concentration (μM) = $\frac{\Delta E_s - \Delta E_b}{\Delta E_{std} - \Delta E_b} \times 10$ The results are shown in Table 5.

TABLE 5

| | WAKO ® Kit (serum: 200 μl) | | Invented method (serum: 50 μl) | |
|---|---|---|---|---|
| Standard liquid | $E_s - E_{sb}$ 0.171 | Bile acid (μM) 50 | $\Delta E_s - E_b$ 0.123 ($\Delta E_{std} - \Delta E_b$) | Bile acid (μM) 10 |
| No. 1 | 0.112 | 32.8 | 0.427 | 34.7 |
| No. 2 | 0.090 | 26.3 | 0.322 | 26.2 |
| No. 3 | 0.071 | 20.8 | 0.261 | 21.2 |
| No. 4 | 0.041 | 12.0 | 0.169 | 13.7 |
| No. 5 | 0.038 | 11.1 | 0.141 | 11.5 |
| No. 6 | 0.030 | 8.77 | 0.120 | 9.78 |
| No. 7 | 0.025 | 7.31 | 0.127 | 10.3 |
| No. 8 | 0.022 | 6.43 | 0.083 | 6.71 |
| No. 9 | 0.019 | 5.56 | 0.063 | 5.11 |
| No. 10 | 0.019 | 5.56 | 0.071 | 5.77 |
| No. 11 | 0.017 | 4.97 | 0.056 | 4.53 |
| No. 12 | 0.017 | 4.97 | 0.060 | 4.87 |
| No. 13 | 0.017 | 4.97 | 0.054 | 4.36 |
| No. 14 | 0.016 | 4.68 | 0.059 | 4.78 |
| No. 15 | 0.015 | 4.39 | 0.049 | 3.96 |
| No. 16 | 0.015 | 4.39 | 0.053 | 4.26 |
| No. 17 | 0.015 | 4.39 | 0.056 | 4.57 |
| $\bar{X}$ (n = 17) | | 9.96 | | 10.4 |

Figure 5:
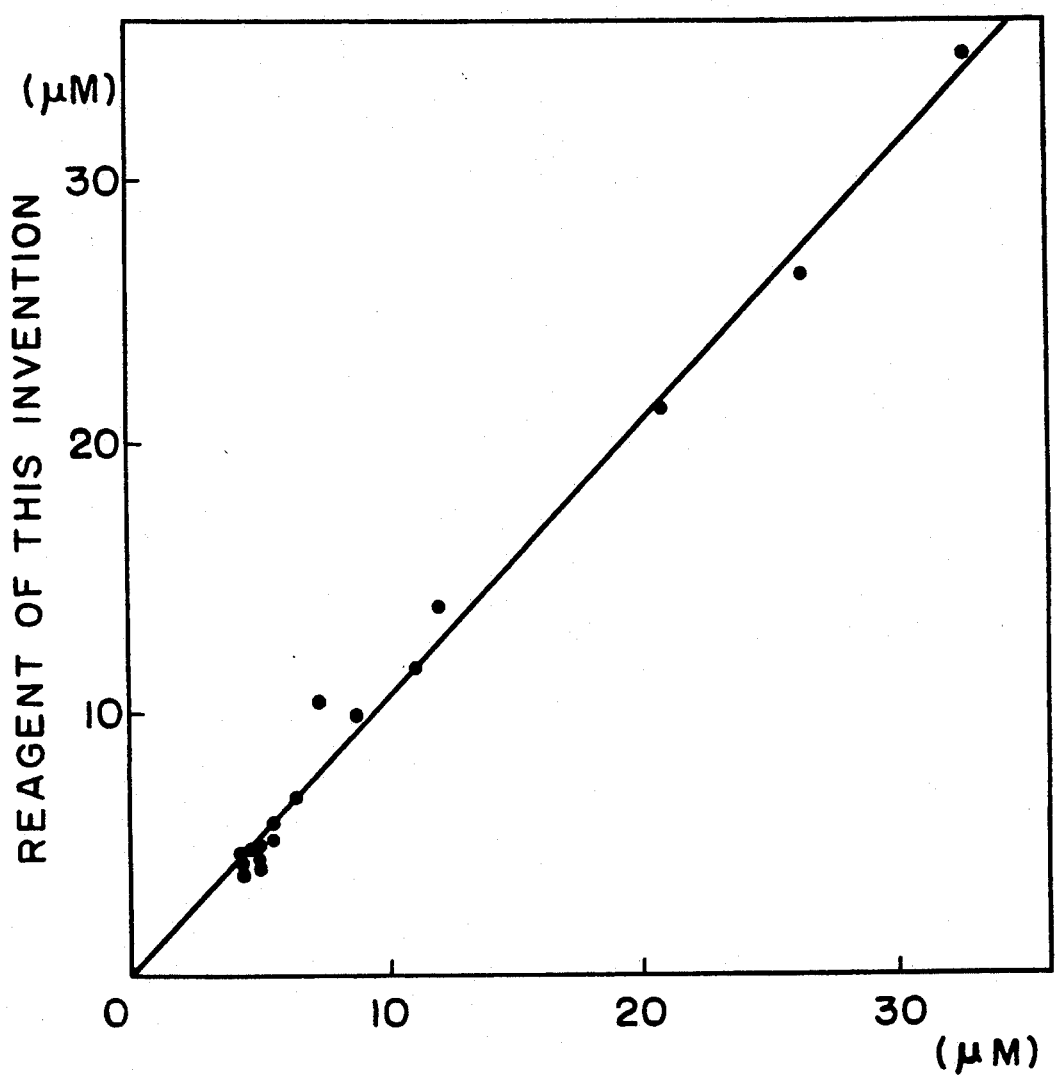
FIG. 5 is a diagram showing the correlation between the reagent composition of the present invention and a commercially available bile acid assay reagent.

A correlation between the reagent of the present invention and the commercially available reagent which is developed based on the data of the above table is given in FIG. 5, which shows that in spite of the smaller amount of sample used in the analysis, i.e., ¼ of that used for the conventional method (50 μl vs. 200 μl), the analysis using the reagent of the present invention exhibited about 4 times or more of absorption than the conventional method using the commercial reagent, thus evidencing the higher sensitivity of the analysis.

Example 9

Reagent 100 mM PIPES-NaOH (pH 7.5)
5 mM acetyl NAD (acetylpyridineadenidinenucleotide)
50 mM NADP
0.2 mM glucose-6-phosphate
5 mM $MgCl_2$
0.2 U/ml glucose-6-phosphate dehydrogenase (derived from yeast, product of Sigma Co.)
25 U/ml 3α-HSD Procedure 1 ml of the above reagent was taken into quartz cuvettes, to which cholic acid was added at different concentrations to produce acetyl NADH. Cholic acid at amounts of 0, 2, 4, 6, 8, and 10 nmol were then measured by absorption changes at 365 nm.

Obviously, numerous modifications and variations of the present invention are possible in light of the above teachings. It is therefore to be understood that within the scope of the appended claims, the invention may be practiced otherwise than as specifically described herein.

What is claimed is:

1. A high-sensitivity method for the quantitative analysis of bile acid in a bile acid-containing sample, said method comprising:
reacting a bile acid-containing sample with a reagent comprising:
   (1) a steroid dehydrogenase which is capable of effecting a reversible reaction producing oxobile acid using bile acid, as a substrate, and a nicotinamide adenine dinucleotide phosphate compound (hereinafter referred to as an NADP compound) or a nicotinamide adenine dinucleotide compound (hereinafter referred to as an NAD compound), as coenzyme,
   (2) compound $A_1$ (defined hereinbelow) in an amount surplus relative to the amount of bile acid,
   (3) compound $B_1$ (defined hereinbelow) or compound $B_2$ (hereinafter defined), or both, wherein the amount of $B_1$ plus $B_2$ is less than 1/100 of the molar amount of $A_1$, and
   (4) a second dehydrogenase which does not react with bile acid and compound $A_1$, but effects a reaction converting compound $B_2$ into compound $B_1$, and the substrate of the second dehydrogenase, to effect the following reaction,

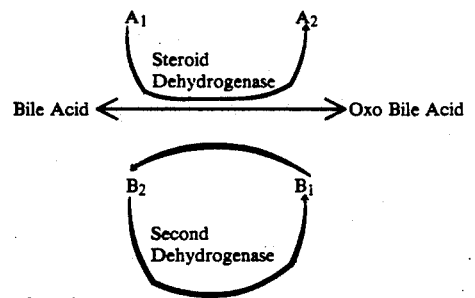

wherein
$A_1$ is an NADP compound or an NAD compound,
$A_2$ is a reduced product of $A_1$,
$B_1$ is a reduced NAD compound, when $A_1$ is an NADP compound, or a reduced NADP compound, when $A_1$ is an NAD compound,
$B_2$ is an oxidized product of $B_1$, and
$B_2 \rightarrow B_1$ indicates a reaction producing $B_1$ using $B_2$ as a coenzyme; and
measuring the amount of $A_2$ produced in the above reaction.

2. The method according to claim 1, wherein the NADP compound is selected from the group consisting of nicotinamide adenine dinucleotide phosphate (NADP), acetylpyridine adenine dinucleotide phosphate (acetyl NADP), and nicotinamide hypoxanthine dinucleotide phosphate (deamino NADP).

3. The method according to claim 1, wherein the NAD compound is selected from the group consisting of nicotinamide adenine dinucleotide (NAD), acetylpyridine adenine dinucleotide (acetyl NAD), and nicotinamide hypoxanthine dinucleotide (deamino NAD).

4. The method according to claim 1, wherein the steroid dehydrogenase is 3α-hydroxysteroid dehydrogenase.

5. The method according to claim 1, wherein the steroid dehydrogenase is 7α-hydroxysteroid dehydrogenase.

6. The method according to claim 1, wherein the steroid dehydrogenase is 12α-hydroxysteroid dehydrogenase.

7. The method according to claim 4, wherein said 3α-hydroxysteroid dehydrogenase is obtained from Pseudomonas sp. B-0831 (FERM BP-2376).

8. The method according to claim 1, wherein the amount of compound $A_1$ to be used is 20–10,000 times in mol of bile acid.

9. A reagent composition for the quantitative analysis of bile acid in a bile acid-containing sample, said reagent composition consisting essentially of:
   (1) a steroid dehydrogenase which is capable of effecting a reversible reaction producing oxobile acid using bile acid, as a substrate, and a nicotinamide adenine dinucleotide phosphate compound (hereinafter referred to as an NADP compound) or a nicotinamide adenine dinucleotide compound (hereinafter referred to as an NAD compound) as coenzyme,
   (2) compound $A_1$ in an amount surplus relative to the amount of bile acid,
   (3) compound $B_1$ or compound $B_2$, or both, wherein the amount of $B_1$ plus $B_2$ is less than 1/100 of the molar amount of $A_1$, and
   (4) a second dehydrogenase which does not react with bile acid and compound $A_1$, but effects a reaction converting compound $B_2$ into compound $B_1$, and the substrate of the second dehydrogenase, wherein $A_1$ is an NADP compound or an NAD compound,
   $B_1$ is a reduced NAD compound when $A_1$ is an NADP compound, or a reduced NADP compound, when $A_1$ is an NAD compound, and
   $B_2$ is an oxidized product of $B_1$.

10. The reagent composition according to claim 9, wherein the NADP compound is selected from the group consisting of nicotinamide adenine dinucleotide phosphate (NADP), acetylpyridine adenine dinucleotide phosphate (acetyl NADP), and nicotinamide hypoxanthine dinucleotide phosphate (deamino NADP).

11. The reagent composition according to claim 9, wherein the NAD compound is selected from the group consisting of nicotinamide adenine dinucleotide (NAD), acetylpyridine adenine dinucleotide (acetyl NAD), and nicotinamide hypoxanthine dinucleotide (deamino NAD).

12. The reagent composition according to claim 9, wherein the steroid dehydrogenase is $3\alpha$-hydroxysteroid dehydrogenase.

13. The reagent composition according to claim 9, wherein the steroid dehydrogenase is $7\alpha$-hydroxysteroid dehydrogenase.

14. The reagent composition according to claim 9, wherein the steroid dehydrogenase is $12\alpha$-hydroxysteroid dehydrogenase.

15. The reagent composition according to claim 12, wherein said $3\alpha$-hydroxysteroid dehydrogenase is obtained from Pseudomonas sp. B-0831 (FERM BP-2376).

16. The reagent composition according to claim 9, wherein said steroid dehydrogenase is present in an amount of 0.05 to 100 U/ml; said compound $A_1$ is present at a concentration of 0.05 to 100 mM; said compounds $B_1$ and $B_2$ are present at a concentration of 0.05 to 500 μM; said second dehydrogenase is present in an amount of 1 to 100 U/ml; and said substrate of said second dehydrogenase is present at a concentration of 0.05 to 50 mM.

17. The reagent composition according to claim 9 wherein, when $B_1$ is a reduced NAD compound, said second dehydrogenase is alcohol dehydrogenase (EC 1.1.1.1), glycerol dehydrogenase (EC 1.1.1.6), glycerol-3-phosphate dehydrogenase (EC 1.1.1.8), malic acid dehydrogenase (EC 1.1.1.37), or glyceraldehyde phosphate dehydrogenase (EC 1.2.1.12).

18. The reagent composition according to claim 9, wherein when $B_1$ is a reduced NAD compound, said second dehydrogenase is glucose-6-phosphate dehydrogenase (EC 1.1.1.49), iso-citric acid dehydrogenase (EC 1.1.1.42), glyoxylic acid dehydrogenase (EC 1.2.1.17), phosphogluconic acid dehydrogenase (EC 1.1.1.44), glyceraldehyde phosphate dehydrogenase (EC 1.2.1.13) or benzaldehyde dehydrogenase (EC 1.2.1.7).

* * * * *